United States Patent
Clemente et al.

(10) Patent No.: US 10,100,325 B2
(45) Date of Patent: Oct. 16, 2018

(54) METHOD FOR THE PRODUCTION OF HIGH SATURATED, LOW POLYUNSATURATED SOYBEAN OIL

(71) Applicant: NUtech Ventures, Lincoln, NE (US)

(72) Inventors: Thomas E. Clemente, Lincoln, NE (US); Hyunwoo Park, Kyeonggi (KR); Edgar Cahoon, Lincoln, MN (US); Hanh Nguyen, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 253 days.

(21) Appl. No.: 14/815,377

(22) Filed: Jul. 31, 2015

(65) Prior Publication Data
US 2016/0040179 A1 Feb. 11, 2016

Related U.S. Application Data

(60) Provisional application No. 62/032,273, filed on Aug. 1, 2014.

(51) Int. Cl.
*C12N 15/82* (2006.01)

(52) U.S. Cl.
CPC .............................. *C12N 15/8247* (2013.01)

(58) Field of Classification Search
None
See application file for complete search history.

(56) References Cited

U.S. PATENT DOCUMENTS

2012/0102587 A1* 4/2012 Anai ........................ A01H 1/04
800/264

OTHER PUBLICATIONS

Allen et al., "Nuclear factors interact with a soybean beta-conglycinin enhancer," Plant Cell. Jun. 1989;1(6):623-31.
Carrington et al., "Cap-independent enhancement of translation by a plant potyvirus 5' nontranslated region," J Virol. Apr. 1990;64(4):1590-7.
Focks et al., "wrinkled1: A Novel, Low-Seed-Oil Mutant of *Arabidopsis* with a Deficiency in the Seed-Specific Regulation of Carbohydrate Metabolism," Plant Physiol. Sep. 1998;118(1):91-101.
Frisch et al., "Chromosomal integration is required for spatial regulation of expression from the β-phaseolin promoter," Plant J., 1995, 7:503-12.
GenBank Accession No. AAA33839.1 Jun. 23, 2010, pp. 1.
GenBank Accession No. AAB51523.1 Jun. 23, 2010, pp. 1.
GenBank Accession No. AAK85232.1 Nov. 30, 2009, pp. 1.
GenBank Accession No. ADK94440.1 Mar. 28, 2012, pp. 1.
GenBank Accession No. ADO16346.1 Oct. 11, 2010, pp. 1.
GenBank Accession No. AFC41106.1 Nov. 19, 2013, pp. 1.
GenBank Accession No. AIL28765.1 Aug. 31, 2014, pp. 1.
GenBank Accession No. CAC80371.1 Feb. 3, 2011, pp. 1.
GenBank Accession No. NM_001250873.1 Feb. 25, 2014, pp. 2.
GenBank Accession No. NM_001251324.1 Mar. 12, 2014, pp. 2.
GenBank Accession No. NM_001251413.1 Mar. 12, 2014, pp. 3.
GenBank Accession No. NP_001292947 Apr. 10, 2015, pp. 1.
GenBank Accession No. NP_189147.1 Jan. 22, 2014, pp. 2.
GenBank Accession No. NP_191000.3 Jan. 22, 2014, pp. 2.
GenBank Accession No. XP_007049712.1 Jul. 10, 2014, pp. 2.
Hawkins et al., "Characterization of acyl-ACP thioesterases of mangosteen (Garcinia mangostana) seed and high levels of stearate production in transgenic canola," Plant J. Mar. 1998;13(6):743-52.
Ivanov et al., "Fatty acid composition of various soybean products," Journal for Institute of Food Technology in Novi Sad, 2010, 37(2):65-70.
Park et al., "Stacking of a stearoyl-ACP thioesterase with a dual-silenced palmitoyl-ACP thioesterase and Δ12 fatty acid desaturase in transgenic soybean," Plant Biotechnol J. Oct. 2014;12(8):1035-43. doi: 10.1111/pbi.12209. Epub Jun. 9, 2014.

* cited by examiner

*Primary Examiner* — Elizabeth F McElwain
(74) *Attorney, Agent, or Firm* — Fish & Richardson P.C.

(57) ABSTRACT

Methods of genetically modifying soybean plants to alter the fatty acid properties of the oil are described.

15 Claims, 6 Drawing Sheets
Specification includes a Sequence Listing.

SEQUENCE LISTING

```
<160> NUMBER OF SEQ ID NOS: 2

<210> SEQ ID NO 1
<211> LENGTH: 1337
<212> TYPE: DNA
<213> ORGANISM: Artificial Sequence
<220> FEATURE:
<223> OTHER INFORMATION: wrinkled 1 sequence from Arabidopsis thaliana
      codon-optimized for expression in soybean

<400> SEQUENCE: 1
ccatgggcat gaaaaagaga cttactacat ccacctgctc ctcgtcgcct tcgtcgtcag      60
tgtcgtcgtc aactacaacc tcgtcgccaa tccagtcaga agccccaagg cctaaacgag     120
ctaagagagc aaagaaatca tccccatccg gcgataagtc tcacaatcca acgtcccctg     180
cttctaccag gcgatcttcg atctataggg gcgttactcg acacagatgg acaggacgat     240
tcgaggcaca tctttgggac aaaagttcat ggaattccat tcaaaacaag aaaggaaagc     300
aggtctatct cggtgcttac gactctgagg aagctgcagc ccatacttat gatcttgctg     360
cattaaagta ctggggacca gacacaatct taaattttcc tgcagaaacg tataccaaag     420
agctcgagga aatgcaaagg gtcactaagg aggaatacct cgcctcactt agaaggcagt     480
cctctggctt ctcgagagga gttagtaaat atagaggtgt cgctaggcat caccataatg     540
gccgatggga agcaaggata ggtcgagtgt ttggcaataa gtatctctac cttggcactt     600
acaacacaca agaggaagcc gctgcagcct atgatatggc tgcaatcgag taccgaggag     660
caaatgccgt tacgaacttc gacatctcaa actacattga tagactcaag aaaaagggag     720 tttttcccatt tcctgtcaat caagcaaacc accaggaagg tattcttgtg gaggcaaagc     780
aagaagtaga gactcgagaa gccaaagagg aaccaagaga ggaagtgaag caacagtatg     840
tagaggaacc acctcaggag gaagaggaaa aagaggaaga gaaggccgag caacaggaag     900
ctgagatcgt tggctactcg gaagaggccg ctgttgtcaa ttgctgtata gactcgagta     960
ccatcatgga gatggaccga tgcggcgata taacgagct cgcatggaat ttttgtatga    1020
tggacacggg attctcccca tttctcaccg atcagaacct tgccaatgag aacccaattg    1080 aatacccctga gctcttcaat gagttagctt ttgaggacaa catagatttc atgtttgacg    1140
atggcaagca tgaatgctta aatctcgaga acctcgattg ctgtgtggta ggaagggagt    1200
caccaccttc atcctcttcg ccattatcgt gtctcagtac cgactcagct agttcaacca    1260
```

```
ctacaactac cacctccgtt tcgtgtaact acctctttca gggtctcttc gttggctcag    1320
aataatctag aatctag                                                   1337

<210> SEQ ID NO 2
<211> LENGTH: 1070
<212> TYPE: DNA
<213> ORGANISM: Artificial Sequence
<220> FEATURE:
<223> OTHER INFORMATION: stearoyl-ACP thioesterase sequence from
      mangosteen codon-optimized for expression in soybean

<400> SEQUENCE: 2
ccatggcact taaactctcc tcatccagaa gcccattggc taggattcct acaagaccta      60
gaccaaacag tattccacca aggatcattg tggtgtcttc ctcttcatct aaggtgaacc     120
cattgaaaac cgaagctgtg gtttccagcg gtttggcaga taggcttaga cttggttctc     180
ttacagagga cggactctca tataaggaga agttcattgt gaggtgctat gaggttggaa     240
ttaacaagac cgctaccgtt gagaccattg caaatttgct tcaagaggtt ggatgtaacc     300
atgctcagtc tgttggatac tcaaccggag gattctctac tacacctaca atgaggaaat     360
tgagactcat ctgggttact gcaaggatgc atatcgagat ctacaaatac cctgcttgga     420
gcgatgttgt ggagattgaa tcttggggac aaggtgaggg aaagatcggt actaggaggg     480
attggattct cagagattat gcaacaggac aggttattgg aagggcaact tccaaatggg     540
ttatgatgaa tcaggatact aggaggctcc aaaaagttga tgtggatgtt agagatgaat     600
accttgttca ttgtccaagg gagcttagac ttgcattccc agaagaaaat aacagtagtc     660
ttaaaaagat cagtaagctc gaggaccccta gtcaatattc aaagttggga cttgttccaa     720
ggagggctga tcttgatatg aatcaacacg ttaacaacgt tacatatatc ggatgggttt     780
tggagagtat gcctcaagag attatcgata cccatgagtt gcaaaccatt accttggatt     840
ataggaggga atgccagcat gacgatgttg tggattctct cacatcccct gaaccatctg     900
aagatgcaga ggcagtgttt aatcacaacg gaactaacgg atctgctaac gtttctgcaa     960
atgaccatgg ttgtagaaac ttcttgcatc tcttgaggct ttcaggaaat ggtttggaga    1020
tcaatagagg aaggactgag tggaggaaga aaccaacaag atagtctaga                1070
```

US 10,100,325 B2

METHOD FOR THE PRODUCTION OF HIGH SATURATED, LOW POLYUNSATURATED SOYBEAN OIL

CROSS REFERENCE TO RELATED APPLICATIONS

This application claims the benefit of priority under 35 U.S.C. § 119(e) to U.S. Application No. 62/032,273 filed Aug. 1, 2014.

FEDERALLY SPONSORED RESEARCH OR DEVELOPMENT

This invention was made with government support under DE-AR0000206 awarded by the U.S. Department of Energy, and 2012-31100-06031 and 2013-31100-06031 awarded by the U.S. Department of Agriculture. The government has certain rights in the invention.

TECHNICAL FIELD

This disclosure generally relates to plants, more specifically, transgenic plants.

BACKGROUND

Soybean oil is one of the most widely consumed cooking oils, and also is used as a base for printing inks and oil paints. Per 100 grams, soybean oil typically contains about 16 grams of saturated fat, about 23 grams of monounsaturated fat, and about 58 grams of polyunsaturated fat (Poth, 2001, "Drying Oils and Related Products," Ullmann's Encyclopedia of Industrial Chemistry). The major unsaturated fatty acids in soybean oil triglycerides are the polyunsaturates, alpha-linolenic acid (C18:3), usually in amounts of about 7-10%, and linoleic acid (C18:2), usually in amounts of about 51%; and the monounsaturate, oleic acid (C18:1), usually in amounts of about 23% (Ivanov et al., 2010, J. Inst. Food Technol. In Novi Sad, 37(2):65-70. Soybean oil also contains the saturated fatty acids, stearic acid, (C18:0), usually in amounts of about 4%, and palmitic acid, (C16:0), usually in amounts of about 10%.

SUMMARY

This disclosure describes methods of genetically modifying soybean plants to alter the fatty acid properties of the oil.

In one aspect, a method of making a transgenic soybean plant is provided. Such a method generally includes expressing a heterologous wrinkled (wri) 1 nucleic acid sequence in a soybean plant. In some embodiments, such a plant further can include expressing a heterologous stearoyl-ACP thioesterase nucleic acid sequence in the soybean plant. In some embodiments, such a plant can further include inhibiting expression of an endogenous FAD2-1 delta-12 fatty acid desaturase in the soybean plant.

In another aspect, a method of making a transgenic soybean plant is provided. Generally, such a method includes expressing a heterologous fatB nucleic acid sequence; expressing a heterologous stearoyl-ACP thioesterase nucleic acid sequence; and inhibiting expression of an endogenous FAD2-1 delta 12 fatty acid desaturase nucleic acid sequence.

In another aspect, a method of making a transgenic soybean plant is provided. Such a method typically includes expressing a heterologous fatB nucleic acid sequence, inhibiting expression of an endogenous delta 9 stearoyl-ACP fatty acid desaturase nucleic acid sequence; and inhibiting expression of an endogenous FAD2-1 delta 12 fatty acid desaturase nucleic acid sequence.

In some embodiments, a nucleic acid sequence as described herein is expressed from a seed-specific promoter. In some embodiments described herein, inhibiting the expression includes expressing a transgene comprising an inhibitory RNA molecule. In some embodiments, the transgene further comprises a seed-specific promoter.

In some embodiments, the transgenic soybean plant includes oil that exhibits an increased amount of palmitic acid relative to a non-transgenic soybean plant. In some embodiments, the transgenic soybean plant includes oil that exhibits an increased amount of stearate relative to a non-transgenic soybean plant. In some embodiments, the transgenic soybean plant comprises oil that exhibits an increased amount of oleate relative to a non-transgenic soybean plant.

In still another aspect, a method of making a soybean plant is provided. Such a method generally includes introducing a mutation into one or more of a stearoyl-ACP thioesterase and a FAD2-1 delta 12 fatty acid desaturase nucleic acid sequence.

Representative mutations include, for example, a point mutation, an insertion, a deletion, a substitution, and combinations thereof. In some embodiments, the soybean plant comprises oil that exhibits an increased amount of palmitic acid relative to a soybean plant lacking the mutations. In some embodiments, the soybean plant comprises oil that exhibits an increased amount of stearic acid relative to a soybean plant lacking the mutations.

In yet another aspect, a transgenic soybean plant is provided. Such a plant typically includes at least two transgenes selected from the group consisting of wrinkled 1, stearoyl-ACP thioesterase, FAD2-1 delta-12 fatty acid desaturase, delta 9 stearoyl-ACP fatty acid desaturase, and fatB, wherein the transgenic soybean plant comprises oil that exhibits a saturated fatty acid content of 25% and an oleic fatty acid content of 40%.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
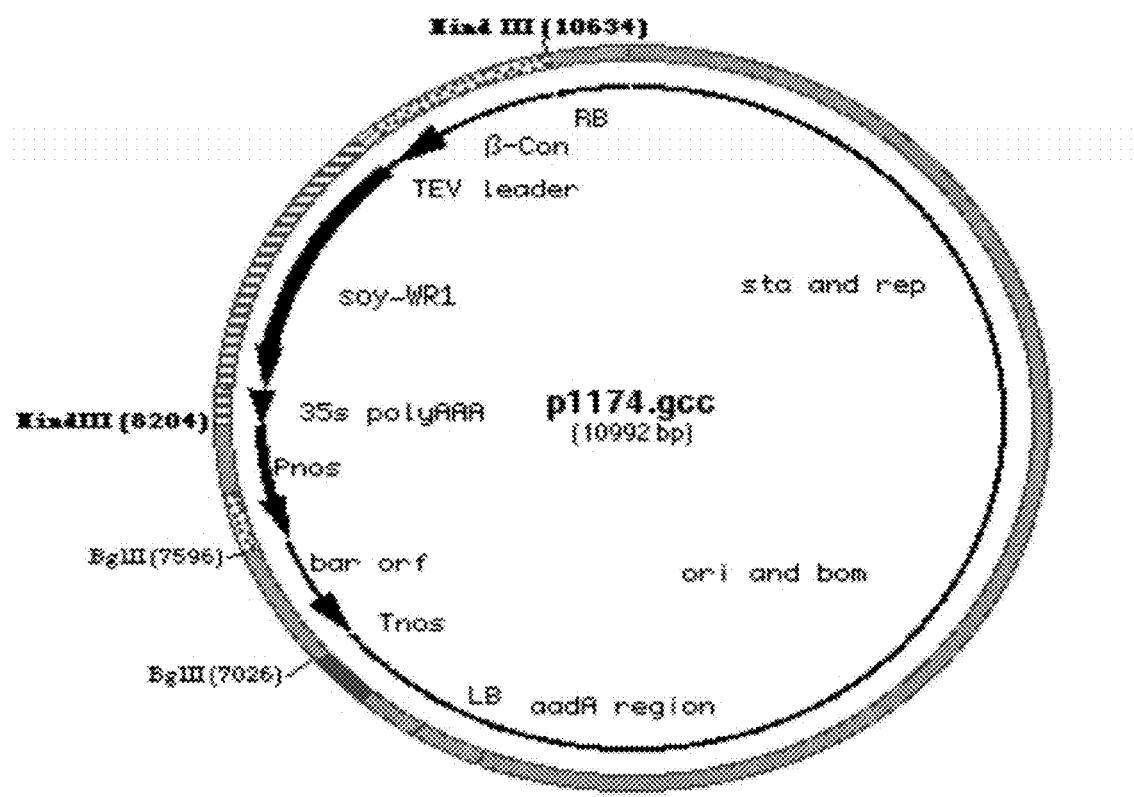
FIG. 1 is a schematic representation of binary vector pPTN1174, which carries a codon-optimized version of the *Arabidopsis* transcription factor wrinkled (wri 1) under control of the seed specific promoter beta conglycinin.

The present disclosure describes methods that can be used to produce soybean plants that contain oil having modified fatty acid properties. For example, soybean plants that produce oil containing significantly increased amount of palmitic acid are described. The present disclosure also describes several different methods that can be used to produce soybean plants that contain oil that is high in saturated fatty acids and low in polyunsaturated fatty acids.

As explained herein, the present disclosure demonstrates the unexpected effects on soybean oil of expressing and/or inhibiting the expression of one or more heterologous genes in a soybean plant including, without limitation, wrinkled 1 (e.g., GenBank Accession No. NP_191000.3 (from *Arabidopsis thaliana*); AD016346.1 (from *Brassica napus*); or NP_001292947 (from *Jatropha curcas*)), stearoyl-ACP thioesterase (e.g., GenBank Accession No. AAB51523.1 (from *Garcinia mangostana*); XP_007049712.1 (from *Theobroma cacao*); or NP_189147.1 (from *Arabidopsis thaliana*)), FAD2-1 delta-12 fatty acid desaturase (e.g., GenBank Accession No. NM_001251413.1 (from *Glycine max*); ADK94440.1 (from *Carthamus tinctorius*); or AFC41106.1 (from *Brassica oleracea*)), delta 9 stearoyl-ACP fatty acid desaturase (GenBank Accession No. NM_001251324.1 (from *Glycine max*); AAK85232.1 (from *Arabidopsis thaliana*); or AAA33839.1 (from *Solanum tuberosum*)), and fatB (e.g., GenBank Accession No. NM_001250873.1 (from *Glycine max*); CAC80371.1 (from *Helianthus annus*); or AIL28765.1 (from *Zea mays*)). In some embodiments, the nucleic acid sequence can be codon optimized for expression in soybean.

Nucleic Acids and Polypeptides

Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use. As used herein, "heterologous" refers to a nucleic acid that is not normally contained within the soybean genome. As used herein, "heterologous" also refers to a soybean nucleic acid that has been introduced into soybean as an additional (i.e., non-naturally occurring) copy.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Nucleic acids can be detected using any number of amplification techniques (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization.

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is oftentimes accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

A construct, sometimes referred to as a vector, containing a nucleic acid (e.g., a coding sequence or an open reading frame) is provided. Constructs, including expression constructs (or expression vectors), are commercially available or can be produced by recombinant DNA techniques routine in the art. A construct containing a nucleic acid can have expression elements operably linked to such a nucleic acid, and further can include sequences such as those encoding a selectable marker (e.g., an antibiotic resistance gene). A construct can encode a chimeric or fusion polypeptide (i.e., a first polypeptide operatively linked to a second polypeptide). Representative first (or second) polypeptides are those that can be used in purification of the other (i.e., second (or first), respectively) polypeptide including, without limitation, 6×His tag or glutathione S-transferase (GST).

Expression elements include nucleic acid sequences that direct and regulate expression of nucleic acid coding sequences. One example of an expression element is a promoter sequence. Promoters that can be used to drive expression of, for example, a coding sequence and/or a selectable marker are known in the art and include, without limitation, constitutive promoters such as, for example, the cassava mosaic virus (CsMVM) promoter, the cauliflower mosaic virus (CaMV) 35S promoter, the actin promoter, or the glyceraldehyde-3-phosphate dehydrogenase promoter, or tissue-specific promoters such as, without limitation, root-specific promoters such as the putrescine N-methyl transferase (PMT) promoter or seed-specific promoters such as the beta-conglycinin promoter from soybean or the phaseolin promoter from common bean. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Constructs as described herein can be introduced into a host cell. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer. As used herein, "host cell" refers to the particular cell into which the nucleic acid is introduced and also includes the progeny or potential progeny of such a cell. A host cell can be any prokaryotic or eukaryotic cell. For example, nucleic acids can be introduced into bacterial cells such as E. coli, or into insect cells, yeast, plant or mammalian cells (such as Chinese hamster ovary cells (CHO) or COS cells). Other suitable host cells are known to those of skill in the art.

RNA Interfering Nucleic Acids and Constructs Containing Same

RNA interference (RNAi), also called post-transcriptional gene silencing (PTGS), is a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). In transgenic plants, the use of RNAi can involve the introduction of long dsRNA (e.g., greater than 50 bps) or siRNAs (e.g., 12 to 23 bps) that have complementarity to the target gene, both of which are processed by the endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery.

A RNAi nucleic acid molecule as described herein is complementary to at least a portion of a target mRNA, and typically is referred to as an "antisense strand". Typically, the antisense strand includes at least 15 contiguous nucleotides of the DNA sequence; it would be appreciated that the antisense strand has the "RNA equivalent" sequence of the DNA (e.g., uracils instead of thymines; ribose sugars instead of deoxyribose sugars).

A RNAi nucleic acid molecule can be, for example, 15 to 500 nucleotides in length (e.g., 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, the "antisense strand" (e.g., a first nucleic acid) can be accompanied by a "sense strand" (e.g., a second nucleic acid), which is complementary to the antisense strand. In the latter case, each nucleic acid (e.g., each of the sense and antisense strands) can be between 15 and 500 nucleotides in length (e.g., between 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, a spacer nucleic acid, sometimes referred to as a loop nucleic acid, can be positioned between the sense strand and the antisense strand. In some embodiments, the spacer nucleic acid can be an intron (see, for example, Wesley et al., 2001, The Plant J., 27:581-90). In some embodiments, although not required, the intron can be functional (i.e., in sense orientation; i.e., spliceable) (see, for example, Smith et al., 2000, Nature, 407:319-20). A spacer nucleic acid can be between 20 nucleotides and 1000 nucleotides in length (e.g., 25-800, 25-600, 25-400, 50-750, 50-500, 50-250, 100-700, 100-500, 100-300, 250-700, 300-600, 400-700, 500-800, 600-850, or 700-1000 nucleotides in length).

In some embodiments, a construct can be produced by operably linking a promoter that is operable in plant cells; a DNA region, that, when transcribed, produces an RNA molecule capable of forming a hairpin structure; and a DNA region involved in transcription termination and polyadenylation. It would be appreciated that the hairpin structure has two annealing RNA sequences, where one of the annealing RNA sequences of the hairpin RNA structure includes a sense sequence identical to at least 20 consecutive nucleotides of the target nucleotide sequence, and where the second of the annealing RNA sequences includes an antisense sequence that is identical to at least 20 consecutive nucleotides of the complement of the target nucleotide sequence. In addition, as indicated herein, the DNA region can include an intron (e.g., a functional intron). When present, the intron generally is located between the two annealing RNA sequences in sense orientation such that it is spliced out by the cellular machinery (e.g., the spliceosome). Such a construct can be introduced into one or more plant cells to reduce the expression of a target nucleic acid (e.g., a nucleic acid sequence that is normally expressed in a plant cell).

In some embodiments, a construct (e.g., an expression construct) can include an inverted-duplication of a segment of a target gene, where the inverted-duplication of the target gene segment includes a nucleotide sequence substantially identical to at least a portion of the target gene and the complement of the portion of the target gene. It would be appreciated that a single promoter can be used to drive expression of the inverted-duplication of the target gene segment, and that the inverted-duplication typically contains at least one copy of the portion of the target gene in the sense orientation. Such a construct can be introduced into one or more plant cells to delay, inhibit or otherwise reduce the expression of a target gene in the plant cells.

It would be appreciated by the skilled artisan that the region of complementarity, between the antisense strand of the RNAi and the mRNA or between the antisense strand of the RNAi and the sense strand of the RNAi, can be over the entire length of the RNAi nucleic acid molecule, or the region of complementarity can be less than the entire length of the RNAi nucleic acid molecule. For example, a region of complementarity can refer to, for example, at least 15 nucleotides in length up to, for example, 500 nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 nucleotides in length). In some embodiments, a region of complementarity can refer to, for example, at least 15 contiguous nucleotides in length up to, for example, 500 contiguous nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 contiguous nucleotides in length).

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides (or amino acid residues) between the two nucleic acids (or polypeptides) is determined. The number of identical matches is divided by the length of the aligned region (i.e., the number of aligned nucleotides (or amino acid residues)) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences (nucleic acid or polypeptide), and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

A construct (also known as a vector) containing a RNAi nucleic acid molecule is provided. Constructs, including expression constructs, are described herein and are known to those of skill in the art. Expression elements (e.g., promoters) that can be used to drive expression of a RNAi nucleic acid molecule are known in the art and include, without limitation, constitutive promoters such as, without limitation, the cassava mosaic virus (CsMVM) promoter, the cauliflower mosaic virus (CaMV) 35S promoter, the actin promoter, or the glyceraldehyde-3-phosphate dehydrogenase promoter, or tissue-specific promoters such as, without limitation, root-specific promoters such as the putrescine N-methyl transferase (PMT) promoter or seed-specific promoters such as the beta-conglycinin promoter from soybean or the phaseolin promoter from common bean. It would be understood by a skilled artisan that a sense strand and an antisense strand can be delivered to and expressed in a target cell on separate constructs, or the sense and antisense strands can be delivered to and expressed in a target cell on a single construct (e.g., in one transcript). As discussed herein, a RNAi nucleic acid molecule delivered and expressed on a single strand also can include a spacer nucleic acid (e.g., a loop nucleic acid) such that the RNAi forms a small hairpin (shRNA).

Transgenic Plants and Methods of Making Transgenic Plants

Transgenic soybean plants (*Glycine max*) are provided that contain a transgene. The transgene can include a coding sequence or an open reading frame, or the transgene can include a RNAi nucleic acid molecule. As discussed herein, the transgene can be delivered in a construct or vector having the appropriate expression elements and other desirable features (e.g., a selectable marker).

When the transgene encodes at least one RNAi molecule, expression of a target gene is inhibited or silenced when the transgene is transcribed. As used herein, inhibiting or silencing can refer to complete elimination or essentially complete elimination of the target mRNA, resulting in 100% or essentially 100% reduction (e.g., greater than 95% reduction; e.g., greater than 96%, 97%, 98% or 99% reduction) in the amount of polypeptide expressed from the target gene; inhibiting or silencing also can refer to partial elimination of the target mRNA (e.g., eliminating about 5%, 10%, 15%, 20%, 25%, 30%, 35%, 40%, 45%, 50% or more of the target mRNA), resulting in a reduction (e.g., about 5%, 10%, 15%, 20%, 25%, 30%, 35%, 40%, 45%, 50% or more, but not complete elimination) in the amount of the polypeptide expressed from the target gene.

Methods of introducing a nucleic acid (e.g., a construct or vector) into plant cells (e.g., soybean cells) are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation.

Following transformation, the transgenic plant cells can be regenerated into transgenic plants. The regenerated transgenic plants can be screened for the presence of the transgene (e.g., a coding sequence or a RNAi nucleic acid molecule) and/or one or more of the resulting phenotypes (e.g., the amount of mRNA or the expressed polypeptide, the amount of one or more fatty acids) using methods described herein, and plants exhibiting the desired phenotype can be selected.

Methods of detecting one or more fatty acids, and methods of determining the amount of one or more fatty acids are known in the art. Oil composition typically is analyzed by extracting fatty acids from seed samples (e.g., at least 10 seeds), which are then hydrolyzed and converted to fatty acid methyl esters. The particular fatty acids present and/or the amounts of particular fatty acids present in the oil can be determined using, for example, high performance liquid chromatography (HPLC) methods (e.g., HPLC—mass spectroscopy (MS) (HPLC-MS) or high performance thin layer chromatography (HPTLC)) or chromatography methods (e.g., gas chromatography/thermal energy analysis (GC/TEA), liquid chromatography/mass spectrometry (LC/MS), and ion chromatography (IC)). See, also, AOCS Official Method Ac 5-41 or Ca 5a-40. It would be appreciated by the skilled artisan that the percentages of fatty acids referred to herein, unless otherwise indicated, are on a weight basis and refer to the percentage of the fatty acid methyl ester relative to the amount of total fatty acid methyl esters in the sample being analyzed.

The transgenic plants described herein typically exhibit an increased amount of one or more fatty acids including, without limitation, palmitic acid, stearic acid, and oleic acid. As used herein, "increased" refers to an increase (e.g., a statistically significant increase) in the amount of one or more fatty acids by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to a corresponding plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

Progeny plants also can be screened for the presence of the transgene and/or the resulting phenotype, and plants exhibiting the desired phenotype can be selected. As described herein, transgenic plants exhibit a particular amount of at least one fatty acid (e.g., compared to a plant lacking the transgene). As described herein, transcription of the transgene results in a plant that exhibits an increased amount of at least one fatty acid relative to a plant not transcribing the transgene. Regenerated transgenic plants can be screened for the expression of the target gene or the amount of one or more fatty acids or other intermediates in fatty acid biosynthesis, compared to the amount in a corresponding non-transgenic plant, and plants having the desired phenotype can be selected.

Transgenic plants exhibiting the desired phenotype can be used, for example, in a breeding program. Breeding is carried out using known procedures. Successful crosses yield $F_1$ plants that are fertile and that can be backcrossed with one of the parents if desired. In some embodiments, a plant population in the $F_2$ generation is screened for the presence of a transgene and/or the resulting phenotype using standard methods (e.g., amplification, hybridization). Selected plants are then crossed with one of the parents and the first backcross ($BC_1$) generation plants are self-pollinated to produce a $BC_1F_2$ population that is again screened. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the transgene and exhibits variant gene expression. Breeder's seed of the selected plant can be produced using standard methods including, for example, field testing.

The results of a plant breeding program using the transgenic plants described herein are novel and useful varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrid varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility where a transgene inhibits microsporogenesis and/or pollen formation, or self-incompatibility. Female parent plants having CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed set on the resulting male sterile plants.

Varieties and lines described herein can be used to form single-cross $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Techniques that are routinely practiced in the art can be used to extract, process, and analyze the oils produced by the soybean plants described herein. See, for example, Bailey's Industrial Oil & Fat Products, 5th Edition, 1996, Vol. 4, John Wiley & Sons, Inc. Typically, plant seeds are cooked, pressed, and extracted to produce crude oil, which is then degummed, refined, bleached, and deodorized. Simply by way of example, soybean seeds can be tempered by spraying them with water to raise the moisture content to, e.g., 8.5%, and flaked using a smooth roller with a gap setting of, e.g., 0.23 to 0.27 mm. Application of heat deactivates enzymes, facilitates further cell rupturing, coalesces the oil droplets, and agglomerates protein particles, all of which facilitate the extraction process.

Soybean oils produced from the transgenic plants described herein can be used in a liquid form in food products and/or for cooking food products. Soybean oils produced from the transgenic plants described herein also can be used to formulate solid fats, such as spreads (e.g., margarines) and shortenings (e.g., all-purpose shortenings). In addition to a soybean oil from the transgenic plants as described herein, a solid fat also can include water, thickening agents such as gelatin, pectin, carrageenans, agar, or starch, milk products such as spray-dried whey, preservatives such as salt, sodium benzoate, potassium sorbate, and lactic acid, antifoam agents such as dimethylpolysiloxane, antioxidants such as tert-butylhydroquinone, butylated hydroxytoluene, and butylated hydroxyanisole, metal chelators such as citric acid, flavor agents, emulsifiers, vitamins, or coloring agents.

Mutant Plants and Methods of Making

Methods of making a plant having a mutation are known in the art. Mutations can be random mutations or targeted mutations. For random mutagenesis, cells (e.g., soybean cells) typically are mutagenized using, for example, a chemical mutagen or ionizing radiation. Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.*, 39(14): 6315-25) or zinc-finger (see, for example, Wright et al., 2005, *The Plant J.*, 44:693-705). Whether random or targeted, a mutation can be a point mutation, an insertion, a deletion, a substitution, or combinations thereof, which are discussed in more detail below.

The resultant variety includes plants having a mutation in an endogenous target nucleic acid encoding a polypeptide sequence. A mutation in an endogenous target gene as described herein typically results in reduced expression or activity of the target sequence, which, in turn, can result in a reduced amount of at least one fatty acid in the mutant plant, an increased amount of at least one fatty acid in the mutant plant, or a combination thereof, depending on the role of the target gene, relative to a plant lacking the mutation. As used herein, "endogenous" refers to a nucleic acid that is naturally occurring within the soybean genome.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Preferably, a mutation in an endogenous nucleic acid results in a plant that exhibits reduced expression or activity of the polypeptide or a reduced amount of at least one fatty acid. Suitable types of mutations in a coding sequence include, without limitation, insertions of nucleotides, deletions of nucleotides, or transitions or transversions in the wild-type coding sequence. Mutations in the coding sequence can result in insertions of one or more amino acids, deletions of one or more amino acids, and/or conservative or non-conservative amino acid substitutions in the encoded polypeptide. In some cases, a coding sequence can have more than one mutation and/or more than one type of mutation.

Insertion or deletion of amino acids in a coding sequence, for example, can disrupt the conformation of the encoded polypeptide. Amino acid insertions or deletions also can disrupt sites important for recognition of binding ligand(s) or substrate(s) or for activity of the polypeptide. It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the polypeptide, introduce a stop codon to produce a truncated polypeptide, or disrupt an active site or domain (e.g., a catalytic site or domain, a binding site or domain) within the polypeptide.

A "conservative amino acid substitution" is one in which one amino acid residue is replaced with a different amino acid residue having a similar side chain (see, for example, Dayhoff et al. (1978, in *Atlas of Protein Sequence and Structure*, 5(Suppl. 3):345-352), which provides frequency tables for amino acid substitutions), and a non-conservative substitution is one in which an amino acid residue is replaced with an amino acid residue that does not have a similar side chain. Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Following mutagenesis, $M_0$ plants are regenerated from the mutagenized cells and those plants, or a subsequent generation of that population (e.g., $M_1$, $M_2$, $M_3$, etc.), can be screened for those carrying a mutation in the target sequence. Screening for plants carrying a mutation in a nucleic acid or polypeptide can be performed directly using methods routine in the art (e.g., hybridization, amplification, nucleic acid sequencing, peptide sequencing, combinations thereof) or by evaluating the phenotype (e.g., the amount of mRNA or expressed polypeptide, the amount of one or more fatty acids). It would be understood that the phenotype of a mutant plant would be compared to a corresponding plant (e.g., having the same varietal background) that lacks the mutation.

An $M_1$ plant may be heterozygous for a mutant allele and exhibit a wild type phenotype. In such cases, at least a portion of the first generation of self-pollinated progeny of such a plant exhibits a wild type phenotype. Alternatively, an $M_1$ plant may have a mutant allele and exhibit a mutant phenotype. Such plants may be heterozygous and exhibit a mutant phenotype due to a phenomenon such as dominant negative suppression, despite the presence of the wild type allele, or such plants may be homozygous due to independently induced mutations in both alleles.

The mutant plants described herein typically exhibit an increased amount of one or more fatty acids including, without limitation, palmitic acid and/or stearic acid. As used herein, "increased" refers to an increase (e.g., a statistically significant increase) in the amount of one or more fatty acids by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to a corresponding plant lacking the mutation(s). As used herein, statistical significance refers to a p-value of less than 0.05, e.g., a p-value of less than 0.025 or a p-value of less than 0.01, using an appropriate measure of statistical significance, e.g., a one-tailed two sample t-test.

A plant carrying a mutant allele can be used in a plant breeding program to create novel and useful lines, varieties and hybrids. Desired plants that possess the mutation can be backcrossed or self-pollinated to create a second population to be screened. Backcrossing or other breeding procedures can be repeated until the desired phenotype of the recurrent parent is recovered. DNA fingerprinting, SNP or similar technologies may be used in a marker-assisted selection (MAS) breeding program to transfer or breed mutant alleles into other lines or varieties, as described herein.

In some embodiments, an $M_1$, $M_2$, $M_3$ or later generation plant containing at least one mutation is crossed with a second plant, and progeny of the cross are identified in which the mutation(s) is present. It will be appreciated that the second plant can be one of the species and varieties described herein. It will also be appreciated that the second plant can contain the same mutation as the plant to which it is crossed, a different mutation, or be wild type at the locus. Additionally or alternatively, a second line can exhibit a phenotypic trait such as, for example, disease resistance, high yield, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Soybean oils produced from the mutant plants described herein can be used in a liquid form in food products and/or for cooking food products. Soybean oils produced from the mutant plants described herein also can be used to formulate solid fats, such as spreads (e.g., margarines) and shortenings (e.g., all-purpose shortenings). In addition to a soybean oil from the mutant plants as described herein, a solid fat also can include water, thickening agents such as gelatin, pectin, carrageenans, agar, or starch, milk products such as spray-dried whey, preservatives such as salt, sodium benzoate, potassium sorbate, and lactic acid, antifoam agents such as dimethylpolysiloxane, antioxidants such as tert-butylhydroquinone, butylated hydroxytoluene, and butylated hydroxyanisole, metal chelators such as citric acid, flavor agents, emulsifiers, vitamins, or coloring agents.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Construction of Binary Vector pPTN1174

To enhance carbon flux towards lipids during soybean seed development, as a means to create a high oil soybean, an *Arabidopsis* transcription factor, shown to be a global regulator of lipid biosynthesis in the model plant and designated wrinkled 1 (At wri 1) (Focks & Benning, 1998, Plant Physiol., 118:91-101), was first introduced into soybean. A soybean codon-optimized version of At wri 1 was synthesized (SEQ ID NO:1) (GenScript; Piscataway, N.J.). The synthetic open reading frame (ORF) was fused to the tobacco etch translational enhancer element (TEV) (Carrington & Freed, 1990, J. Virol., 64:1590-7) and subsequently cloned between the soybean seed specific promoter, beta conglycinin (Allen et al., 1989, Plant Cell, 1:623-31) and the 35S CaMV terminator of transcription. The resultant expression cassette was sub-cloned into the binary plasmid pPTN200 which harbors a bar gene (Thompson et al., 1987, EMBO, 6:2519-23) cassette for in vitro selection of transgenic soybean events (Zhang et al., 1999, Plant Cell. Tiss. Org. Cult., 56:37-46; Xing et al., 2000, In Vitro Cell. Dev. Biol., 36:456-63). The final binary vector was designated pPTN1174 (FIG. 1).

```
                                               (SEQ ID NO: 1)
CCATGGGCATGAAAAAGAGACTTACTACATCCACCTGCTCCTCGTCG

CCTTCGTCGTCAGTGTCGTCGTCAACTACAACCTCGTCGCCAATCCA

GTCAGAAGCCCCAAGGCCTAAACGAGCTAAGAGAGCAAAGAAATCAT

CCCCATCCGGCGATAAGTCTCACAATCCAACGTCCCTGCTTCTACC

AGGCGATCTTCGATCTATAGGGCGTTACTCGACACAGATGGACAGG

ACGATTCGAGGCACATCTTTGGGACAAAAGTTCATGGAATTCCATTC

AAAACAAGAAAGGAAAGCAGGTCTATCTCGGTGCTTACGACTCTGAG

GAAGCTGCAGCCCATACTTATGATCTTGCTGCATTAAAGTACTGGGG

ACCAGACACAATCTTAAATTTTCCTGCAGAAACGTATACCAAAGAGC

TCGAGGAAATGCAAAGGGTCACTAAGGAGGAATACCTCGCCTCACTT

AGAAGGCAGTCCTCTGGCTTCTCGAGAGGAGTTAGTAAATATAGAGG

TGTCGCTAGGCATCACCATAATGGCCGATGGGAAGCAAGGATAGGTC

GAGTGTTTGGCAATAAGTATCTCTACCTTGGCACTTACAACACACAA

GAGGAAGCCGCTGCAGCCTATGATATGGCTGCAATCGAGTACCGAGG

AGCAAATGCCGTTACGAACTTCGACATCTCAAACTACATTGATAGAC

TCAAGAAAAGGGAGTTTTCCCATTTCCTGTCAATCAAGCAAACCAC

CAGGAAGGTATTCTTGTGGAGGCAAAGCAAGAAGTAGAGACTCGAGA

AGCCAAAGAGGAACCAAGAGAGGAAGTGAAGCAACAGTATGTAGAGG

AACCACCTCAGGAGGAAGAGGAAAAAGAGGAAGAGAAGGCCGAGCAA

CAGGAAGCTGAGATCGTTGGCTACTCGGAAGAGGCCGCTGTTGTCAA
```

-continued
```
TTGCTGTATAGACTCGAGTACCATCATGGAGATGGACCGATGCGGCG

ATAATAACGAGCTCGCATGGAATTTTTGTATGATGGACACGGGATTC

TCCCCATTTCTCACCGATCAGAACCTTGCCAATGAGAACCCAATTGA

ATACCCTGAGCTCTTCAATGAGTTAGCTTTTGAGGACAACATAGATT

TCATGTTTGACGATGGCAAGCATGAATGCTTAAATCTCGAGAACCTC

GATTGCTGTGTGGTAGGAAGGGAGTCACCACCTTCATCCTCTTCGCC

ATTATCGTGTCTCAGTACCGACTCAGCTAGTTCAACCACTACAACTA

CCACCTCCGTTTCGTGTAACTACCTCTTTCAGGGTCTCTTCGTTGGC

TCAGAATAATCTAGAatctag
```

Example 2—Evaluating Transgenic Plants

Figure 2:
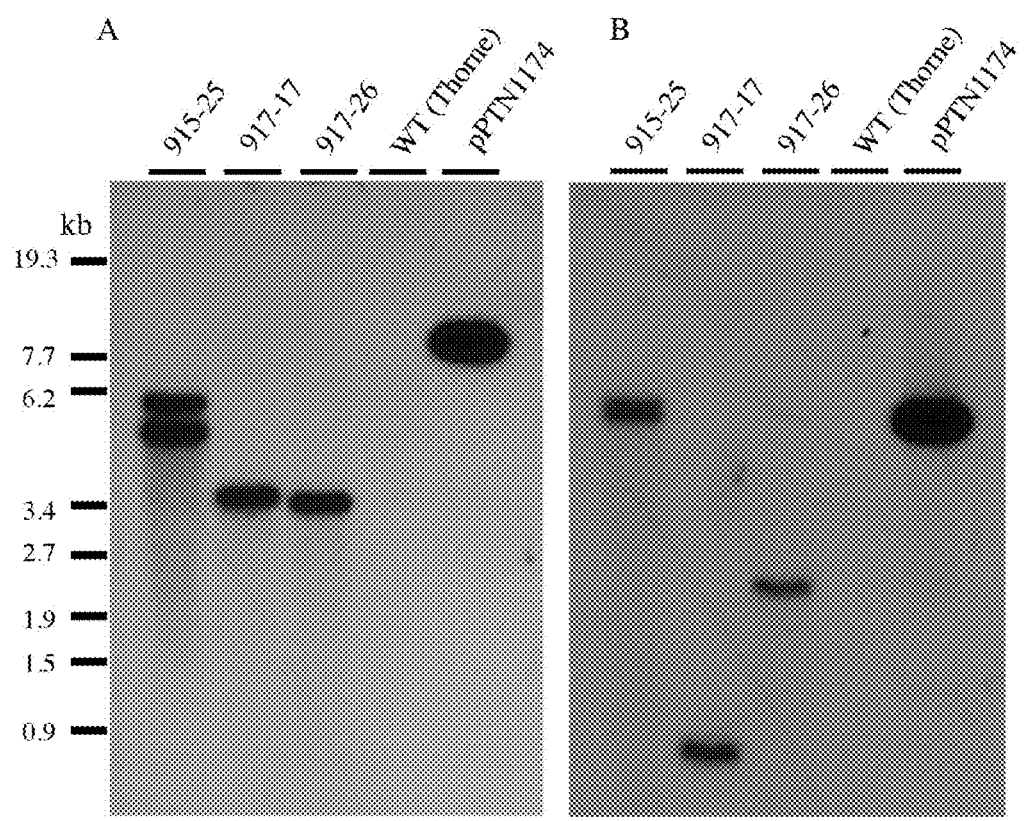
FIG. 2 shows a Southern blot analysis done on three independent transgenic soybean events derived from transformations with pPTN1174. Genomic DNA was digested with BglII and HindIII and hybridized with a probe to the wrinkled gene (Panel A) or a probe to the bar gene (Panel B).

Three independent transgenic soybean events were characterized at the molecular level via Southern blot analysis (FIG. 2). Progeny derived from these lineages were subsequently evaluated for total oil content under greenhouse conditions. Although some variation in total oil content was observed, there was no consistent, significant increase observed.

However, we unexpectedly observed a drastic increase in the amount of palmitic acid (16:10) over control soybeans grown under equivalent greenhouse environmental conditions (Table 1). These transgenic plants exhibited a mean percentage of palmitate that reached 20%.

TABLE 1

Fatty acid profile of soybean seed expressing At wri 1 transgene

| Event | 16:0 | 18:0 | 18:1 | 18:2 | 18:3 |
|---|---|---|---|---|---|
| Thorne #1 | 12.97 ± 0.52 | 3.27 ± 0.71 | 11.76 ± 2.01 | 55.35 ± 3.00 | 16.08 ± 2.37 |
| Thorne #2 | 12.79 ± 0.60 | 3.38 ± 0.22 | 13.82 ± 1.82 | 54.75 ± 1.22 | 14.73 ± 2.51 |
| 915-25-T1-1 | 21.49 ± 1.25 | 2.24 ± 0.22 | 10.46 ± 1.65 | 54.77 ± 1.46 | 10.32 ± 1.20 |
| 915-25-T1-3 | 19.37 ± 1.14 | 2.17 ± 0.17 | 9.25 ± 0.97 | 58.21 ± 2.26 | 10.32 ± 1.53 |
| 917-17-T1-3 | 20.39 ± 1.86 | 2.75 ± 0.33 | 8.75 ± 1.43 | 54.86 ± 3.01 | 12.59 ± 2.75 |
| 917-17-T1-7 | 20.00 ± 2.35 | 2.91 ± 0.23 | 9.69 ± 0.59 | 52.90 ± 2.14 | 13.92 ± 2.32 |
| 917-26-T1-3 | 19.74 ± 0.73 | 2.98 ± 0.15 | 9.24 ± 0.65 | 55.15 ± 0.44 | 12.35 ± 1.09 |

Event column refers to soybean lineage (Thorne control).
16:0, 18:0, 18:1, 18:2 and 18:3 columns represent mean percent ± standard deviation of palmitic acid, stearic acid, oleic acid, linoleic acid, and linolenic acid, respectively.

Figure 3:
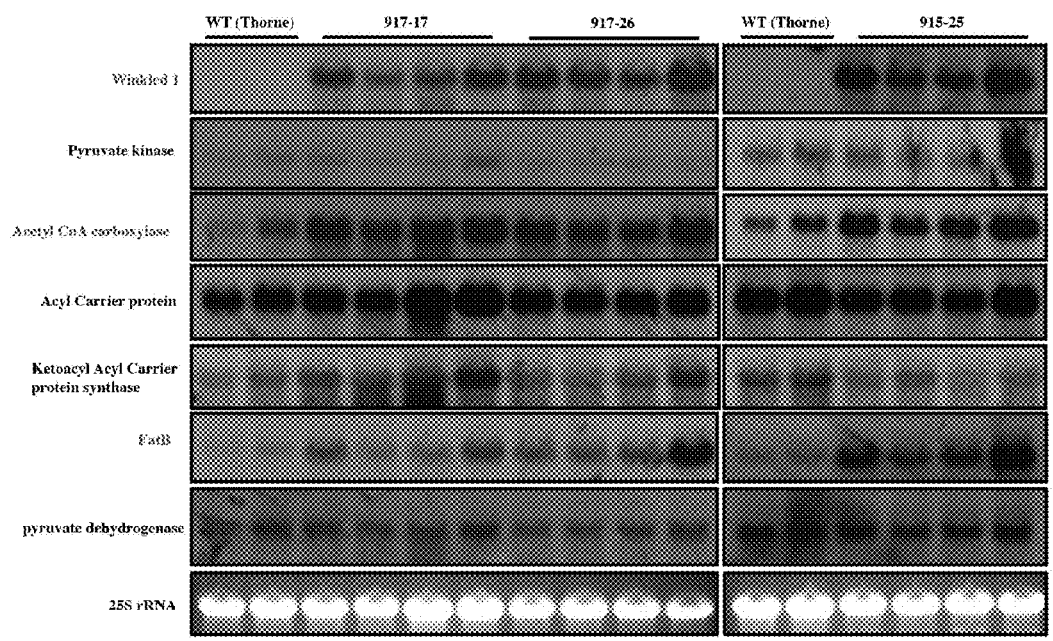
FIG. 3 shows a Northern blot analyses on immature embryo derived from 917-17 and 917-26 events. RNA was extracted from immature embryo and 15 μg of RNA was used. The probe used in the hybridization is shown on the left. Lane 1 and 2, wild type soybean immature embryo. Lane 3 thru 6, immature embryos derived from 917-17 and 917-26 events.

Transcript accumulation was monitored in immature embryos derived from these three wri 1 transgenic events via Northern blot analysis for At wri 1, pyruvate kinase, acetyl CoA carboxylase, acyl carrier protein, ketoacyl-ACP synthase, palmitoyl preferred thioesterase (FatB) and pyruvate dehydrogenase. The data revealed strong accumulation of the transgenic At wri 1 transcript, along with induction of the acetyl CoA carboxylase and FatB (FIG. 3), with the latter likely resulting in the observed increase in palmitate in the seed oil.

Example 3—Transgenic Plants Containing Multiple Transgenes

Given the unexpected results observed with At wri 1 expression in soybean, a genetic approach was pursued to produce a high saturated, low polyunsaturated soybean oil with functionality suitable for baking applications. To this end, the At wri 1 transgenic allele was stacked with a transgenic cassette that harbors the mangosteen stearoyl-ACP thioesterase (Hawkins & Kridl, 1998, Plant J., 13:743-52) codon-optimized for expression in soybean (SEQ ID NO:2) under control of a seed specific promoter (Park et al., 2014, Plant Biotechnol. J., doi: 10.1111/pbi.12209). Expression of the mangosteen thioesterase increases stearate to over 13%, which concomitantly slightly reduces palmitic acid levels in the oil.

```
                                          (SEQ ID NO: 2)
ccATGgcaCTTAAACTCTCCTCATCCAGAAGCCCATTGGCTAGGATT

CCTACAAGACCTAGACCAAACAGTATTCCACCAAGGATCATTGTGGT

GTCTTCCTCTTCATCTAAGGTGAACCCATTGAAAACCGAAGCTGTGG

TTTCCAGCGGTTTGGCAGATAGGCTTAGACTTGGTTCTCTTACAGAG

GACGGACTCTCATATAAGGAGAAGTTCATTGTGAGGTGCTATGAGGT

TGGAATTAACAAGACCGCTACCGTTGAGACCATTGCAAATTTGCTTC

AAGAGGTTGGATGTAACCATGCTCAGTCTGTTGGATACTCAACCGGA

GGATTCTCTACTACACCTACAATGAGGAAATTGAGACTCATCTGGGT

TACTGCAAGGATGCATATCGAGATCTACAAATACCCTGCTTGGAGCG

ATGTTGTGGAGATTGAATCTTGGGGACAAGGTGAGGGAAAGATCGGT

ACTAGGAGGGATTGGATTCTCAGAGATTATGCAACAGGACAGGTTAT

TGGAAGGGCAACTTCCAAATGGGTTATGATGAATCAGGATACTAGGA

GGCTCCAAAAAGTTGATGTGGATGTTAGAGATGAATACCTTGTTCAT

TGTCCAAGGGAGCTTAGACTTGCATTCCCAGAAGAAAATAACAGTAG
```

-continued
```
TCTTAAAAAGATCAGTAAGCTCGAGGACCCTAGTCAATATTCAAAGT

TGGGACTTGTTCCAAGGAGGGCTGATCTTGATATGAATCAACACGTT

AACAACGTTACATATATCGGATGGGTTTTGGAGAGTATGCCTCAAGA

GATTATCGATACCCATGAGTTGCAAACCATTACCTTGGATTATAGGA

GGGAATGCCAGCATGACGATGTTGTGGATTCTCTCACATCCCCTGAA

CCATCTGAAGATGCAGAGGCAGTGTTTAATCACAACGGAACTAACGG

ATCTGCTAACGTTTCTGCAAATGACCATGGTTGTAGAAACTTCTTGC

ATCTCTTGAGGCTTTCAGGAAATGGTTTGGAGATCAATAGAGGAAGG

ACTGAGTGGAGGAAGAAACCAACAAGAtagtctaga
```

In soybean lineages harboring the transgene stack, the fatty acid profile either maintained or slightly increased palmitic acid levels, while enhancing stearic acid levels above 20%, or led to dual enhancement of both palmitic and stearic acids, with a shift towards palmitic acid. In both cases, total saturated fatty acids were between about 25% to about 35% (Table 2).

TABLE 2

Stacking of the mangosteen stearoyl-ACP thioesterase and At wri 1 transgenes in soybean

| Event | 16:0 | 18:0 | 18:1 | 18:2 | 18:3 |
|---|---|---|---|---|---|
| Thorne | 13.03 ± 0.62 | 3.47 ± 0.14 | 13.95 ± 1.17 | 55.77 ± 1.59 | 13.20 ± 1.64 |
| 683-2 | 8.54 ± 0.35 | 17.39 ± 1.04 | 9.72 ± 0.88 | 47.00 ± 1.37 | 15.82 ± 1.41 |
| 687-2 | 9.32 ± 1.04 | 13.14 ± 2.30 | 11.17 ± 2.04 | 48.24 ± 1.37 | 16.68 ± 1.65 |
| 915-25-T1-1 | 21.49 ± 1.25 | 2.24 ± 0.22 | 10.46 ± 1.65 | 54.77 ± 1.46 | 10.32 ± 1.20 |
| 917-17-T1-8 | 21.86 ± 1.84 | 3.35 ± 0.30 | 8.87 ± 1.01 | 50.83 ± 3.80 | 14.43 ± 2.94 |
| 683-2 T3-4 × 915-25 | 14.11 ± 0.00 | 21.19 ± 0.00 | 7.89 ± 0.00 | 39.60 ± 0.00 | 15.05 ± 0.00 |
| 917-17 T1-8 × 683-2 | 10.29 ± 2.00 | 23.15 ± 2.48 | 8.14 ± 0.87 | 36.06 ± 4.49 | 17.01 ± 0.85 |
| 687-2 T4-3 × 915-25 | 17.17 ± 0.73 | 9.94 ± 0.70 | 10.28 ± 0.28 | 47.08 ± 1.20 | 14.12 ± 1.18 |
| 917-17 T1-8 × 687-2 | 18.00 ± 0.41 | 9.33 ± 1.05 | 7.48 ± 0.41 | 43.26 ± 3.45 | 18.80 ± 1.62 |

Even column refers to soybean lineage (Thorne control). 683-2 and 687-2 Events carry mangosteen stearoyl-ACP thioesterase transgene. Events 915-25 and 917-17 harbor the At wri 1 transgenic allele, while the bottom four event designations are transgenic stacks thereof in which the stearoyl-ACP thioesterase and At wri 1 alleles were stacked by crossing.
Columns 16:0, 18:0, 18:1, 18:2, and 18:3 columns represent mean percent ± standard deviation of palmitic acid, stearic acid, oleic acid, linoleic acid, and linolenic acid, respectively.

Example 4—High Saturated, Low Polyunsaturated Soybean Oil

Figure 4:
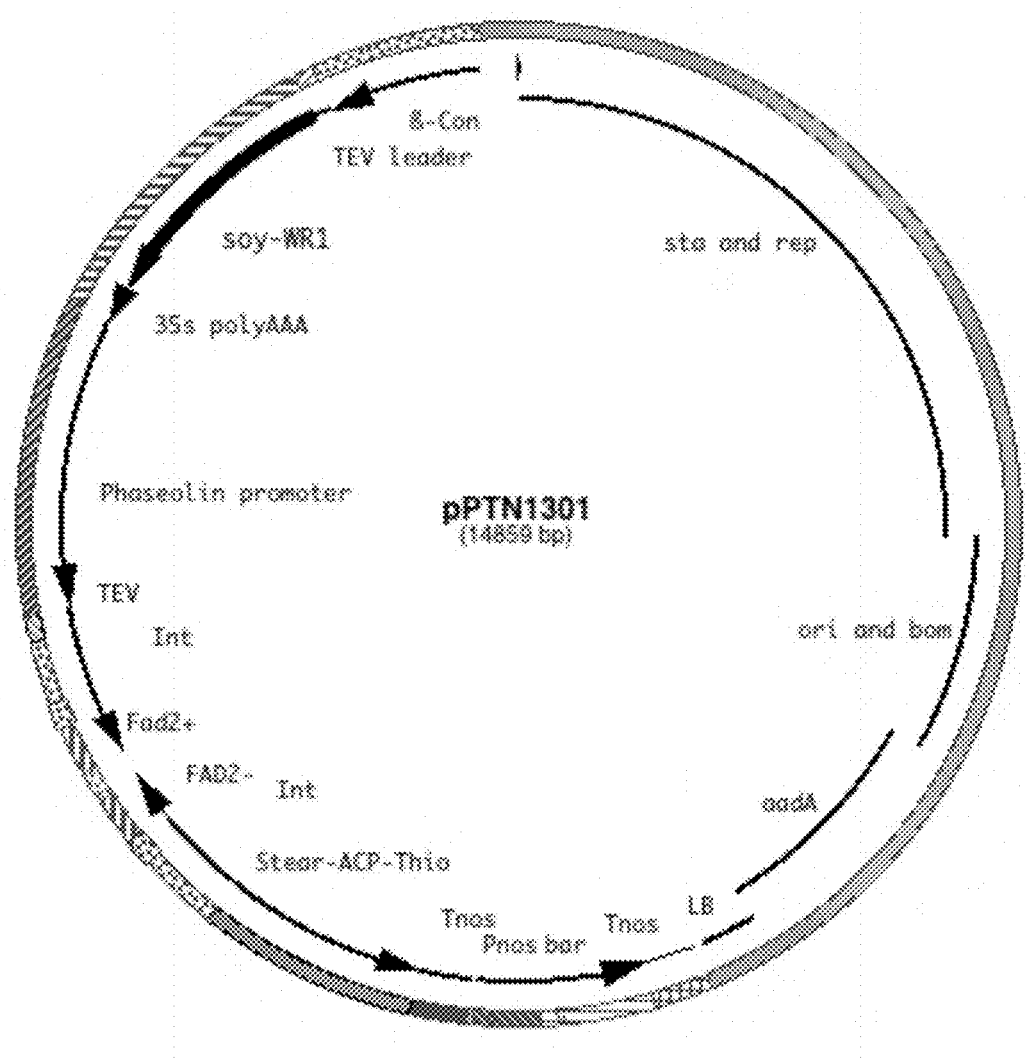
FIG. 4 is a schematic representation of a binary vector designed to simultaneously raise saturated fatty acids and enhance oleic acid content of soybean oil.
Figure 5:
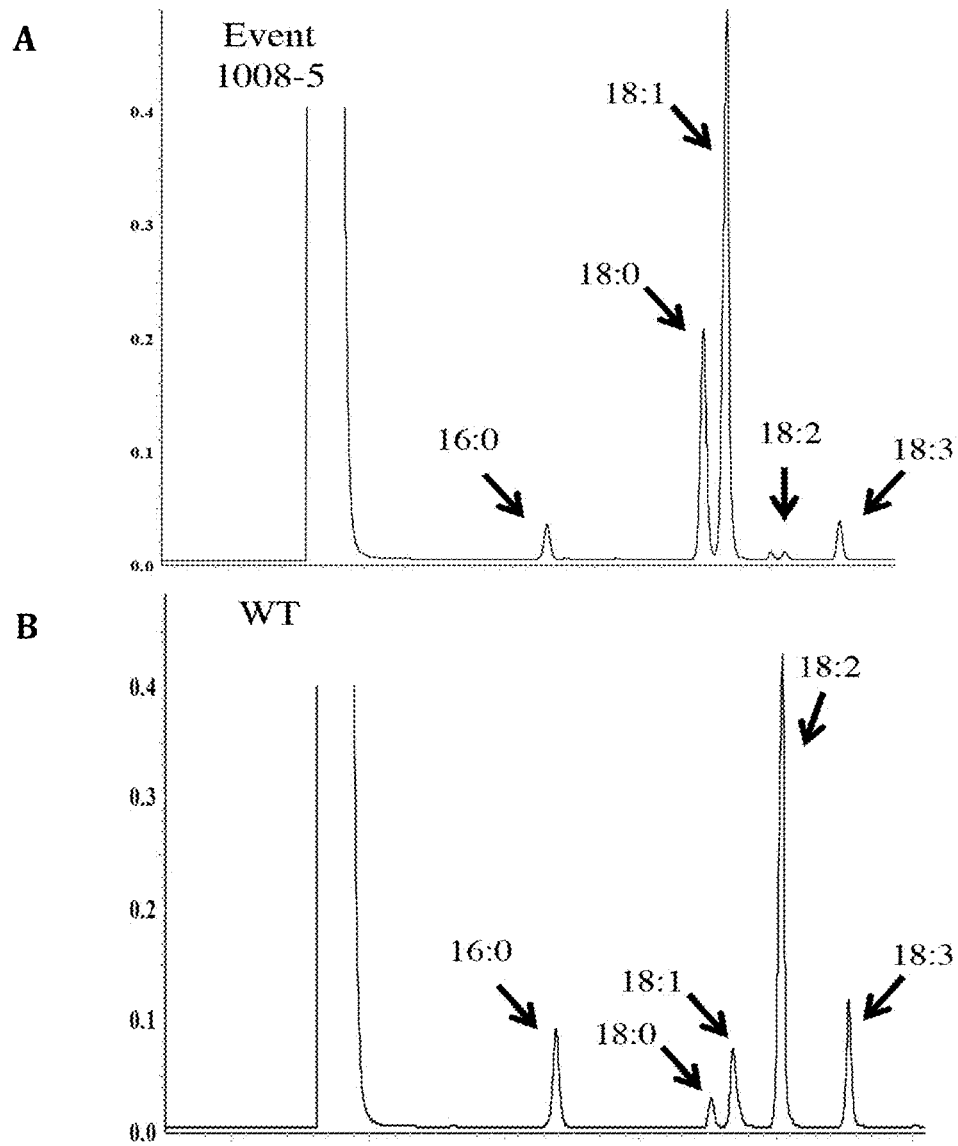
FIG. 5 is a gas chromatograph trace of soybean oil sample derived from Event 1008-5 (Panel A) and wild type (Panel B). Arrows highlight peaks associated with 16:0 (palmitic acid), 18:0 (stearic acid), 18:1 (oleic acid), 18:2 (linoleic acid), and 18:3 (linolenic acid).
Figure 6:
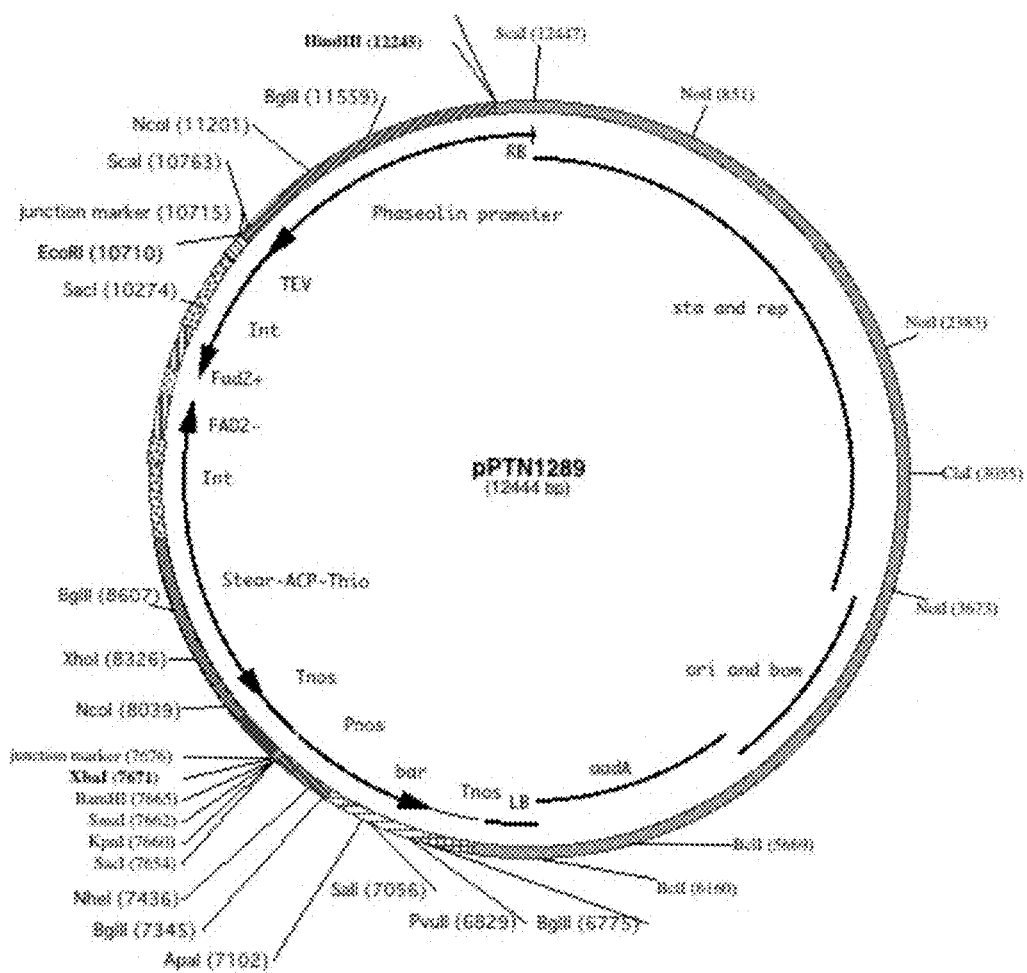
FIG. 6 is a schematic representation of the T-DNA element of pPTN1289, which harbors a novel plant expression cassette design wherein under the control of a single promoter, one can obtain simultaneous down-regulation of an endogenous gene, and expression of an unrelated transgenes. Herein, the phaseolin promoter from common bean is fused to the tobacco etch translational enhancer element (TEV). Immediately downstream resides an RNAi hairpin element targeting down-regulation of the soybean fatty acid desaturase gene FAD2-1 (Fad2), with the soybean small subunit of rubisco intron separating the inverted Fad2 repeats. The Fad2 RNAi hairpin is embedded within the *Arabidopsis* small nuclear riboprotein intron (Int). The mangosteen stearoyl-ACP thioesterase gene (Stear-ACP-Thio) is situated downstream of the Fad2 hairpin embedded within the intron, which is terminated by the Tnos poly-AAA element.

The goal was to create soybean oil in which saturated fatty acids are greater than 25%, coupled with oleic acid accumulation greater than 50%. Towards reaching this target, a novel genetic construct was designed in which a hair-pin element was embedded within an intron, upstream of the mangosteen thioesterase open reading frame, regulated by the phaseolin seed-specific promoter from common bean (Frisch et al., 1995, Plant J., 7:503-12). Thus, expression of this cassette during soybean seed development processes the intron, which, in turn, creates a hairpin, leading to the formation of interfering RNA (RNAi) directed against the FAD2-1 delta-12 fatty acid desaturase gene. Hence, this single cassette leads to enhanced oleate and stearate levels in the seed. To maintain and/or concomitantly enhance palmitate, the construct also harbors the At wri 1 cassette under control of the soybean beta-conglycinin promoter. This binary vector was designated pPTN1301 (FIG. 4).

Soybean plants have been transformed with this binary vector, and transgenic soybean events have been established in the greenhouse.

TABLE 3

Triple stack in soybean combining transgenic alleles

| Event/Linkage | 16:0 | 18:0 | 18:1 | 18:2 | 18:3 |
|---|---|---|---|---|---|
| 683-2 × 915-25 × 374-1 | 9.9 | 15.8 | 56.7 | 9.3 | 7.2 |
| 683-2 × 915-25 × 374-1 | 10.8 | 18.3 | 54.4 | 10.9 | 4.5 |
| 683-2 × 915-25 × 374-1 | 9.0 | 19.1 | 57.8 | 8.8 | 4.3 |
| 683-2 × 915-25 × 374-1 | 10.1 | 23.5 | 51.2 | 9.5 | 4.7 |

Event/Lineage column indicates selected events crossed to create triple stack. 683-2 carries mangosteen stearoyl-ACP thioesterase, 915-25 harbors At wri 1 cassette, while 374-1 has a silencing allele targeting down regulation of the delta12-fatty acid desaturase (FAD2-1). The columns 16:0, 18:0, 18:1, 18:2, and 18:3 has percent level of palmitic acid, stearic acid, oleic acid, linoleic acid, and linolenic acid, respectively.

Example 5—Transgenic Soybean Plants Having Altered Fatty Acid Profiles

The genetic cassette harbored within pPTN1289 carries the mangosteen thioesterase open reading frame, with a 5' hair-pin element designed to down-regulate expression of the soybean FAD2-1 fatty acid desaturase gene. Hence, within a single cassette, driven by one promoter, beta-phaseolin from common bean (Phaseolus vulgarus), a simultaneous silencing of FAD2-1 and expression of the mangosteen thioesterase occurs, translating to a high oleic acid, elevated stearic acid, and a reduction in palmitic acid (Table 4). The binary plasmid, pPTN1301, is the result of an assembly of a three genetic element stack within a single T-DNA to recapitulate the triple stack lineage shown in Table 3. A representative fatty acid profile of soybean, derived from transformations with this plasmid, is shown in Table 5. What is observed is co-expressing wrinkled-1 mitigates the reduction in palmitic acid relative to that observed in the two genetic stack that resides in pPTN1289 (Table 4), thereby elevating the total saturates within the oil and improving functionality for applications requiring a vegetable oil high in saturated fatty acids and low in polyunsaturated fatty acids.

TABLE 4

Fatty acid profile of soybean carrying T-DNA of pPTN1289

| Event | 16:0 | 18:0 | 18:1 | 18:2 | 18:3 |
|---|---|---|---|---|---|
| 1005-5 | 4.1 ± 0.4 | 17.7 ± 3.0 | 69.1 ± 2.3 | 1.3 ± 0.2 | 3.5 ± 0.9 |
| 1005-6 | 5.5 ± 1.1 | 15.8 ± 6.1 | 64.7 ± 7.9 | 3.3 ± 2.6 | 6.3 ± 2.8 |
| 1008-5 | 4.9 ± 0.5 | 17.3 ± 3.7 | 66.3 ± 2.4 | 1.6 ± 0.4 | 5.1 ± 0.9 |
| WT | 12.9 ± 0.5 | 3.6 ± 0.2 | 12.2 ± 1.8 | 53.3 ± 1.1 | 15.5 ± 1.8 |

Event column indicates transgenic event and control (WT) seed samples.
Column 16:0, 18:0, 18:1, 18:2, and 18:3, refer to mean percentages of palmitic acid, stearic acid, oleic acid, linoleic acid, and linolenic acid, respectively, within the seed oil, ± standard deviation. Means were ascertained from 4-8 samples.

TABLE 5

Fatty acid profile of soybean carrying T-DNA of pPTN1301

| Event | 16:0 | 18:0 | 18:1 | 18:2 | 18:3 |
|---|---|---|---|---|---|
| 1026-1 | 7.0 ± 0.5 | 19.4 ± 3.0 | 62.5 ± 2.0 | 2.2 ± 0.8 | 4.8 ± 0.4 |

TABLE 5-continued

Fatty acid profile of soybean carrying T-DNA of pPTN1301

| Event | 16:0 | 18:0 | 18:1 | 18:2 | 18:3 |
|---|---|---|---|---|---|
| 1018-4 | 7.5 ± 0.8 | 16.7 ± 2.1 | 64.7 ± 1.0 | 2.4 ± 0.6 | 4.6 ± 0.3 |
| WT | 13.0 ± 0.5 | 3.3 ± 0.2 | 13.2 ± 0.5 | 52.4 ± 1.5 | 16.3 ± 1.5 |

Event column indicates transgenic event and control (WT) seed samples.
Column 16:0, 18:0, 18:1, 18:2, and 18:3, refer to mean percentages of palmitic acid, stearic acid, oleic acid, linoleic acid, and linolenic acid, respectively, within the seed oil, ± standard deviation. Means were ascertained from 4 samples.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of making a transgenic soybean plant, comprising expressing a heterologous nucleic acid sequence encoding a wrinkled (wri) 1 polypeptide in a soybean plant, wherein the heterologous nucleic acid sequence encoding the wri 1 polypeptide has at least 95% sequence identity to the nucleic acid sequence shown in SEQ ID NO:1; expressing a heterologous nucleic acid sequence encoding a stearoyl-ACP thioesterase polypeptide in the soybean plant; and inhibiting expression of an endogenous FAD2-1 delta-12 fatty acid desaturase nucleic acid in the soybean plant.

2. The method of claim 1, wherein the nucleic acid sequence encoding the wri 1 polypeptide is expressed from a seed-specific promoter.

3. The method of claim 1, wherein inhibiting the expression comprises expressing a transgene comprising an inhibitory RNA molecule.

4. The method of claim 3, wherein the transgene further comprises a seed-specific promoter.

5. The method of claim 1, wherein the transgenic soybean plant comprises oil that exhibits a decreased amount of palmitic acid relative to a non-transgenic soybean plant.

6. The method of claim 1, wherein the transgenic soybean plant comprises oil that exhibits an increased amount of stearate relative to a non-transgenic soybean plant.

7. The method of claim 1, wherein the transgenic soybean plant comprises oil that exhibits an increased amount of oleate relative to a non-transgenic soybean plant.

8. The method of claim 1, wherein the transgenic soybean plant comprises oil that exhibits an increased amount of saturated fatty acids and a decreased amount of polyunsaturated fatty acids relative to a non-transgenic soybean plant.

9. The method of claim 1, wherein the heterologous wrinkled (wri) 1 nucleic acid sequence has the nucleic acid sequence shown in SEQ ID NO:1.

10. The method of claim 1, wherein the heterologous stearoyl-ACP thioesterase nucleic acid sequence has at least 95% sequence identity to the nucleic acid sequence shown in SEQ ID NO:2.

11. The method of claim 1, wherein the heterologous stearoyl-ACP thioesterase nucleic acid sequence has the nucleic acid sequence shown in SEQ ID NO:2.

12. The method of claim 1, wherein inhibiting the expression comprises introducing a mutation into the endogenous FAD2-1 delta-12 fatty acid desaturase nucleic acid.

13. The method of claim 1, wherein the nucleic acid sequence encoding the stearoyl-ACP thioesterase polypeptide is expressed from a seed-specific promoter.

14. The method of claim 1, wherein the nucleic acid sequence encoding the wri 1 polypeptide is expressed from a seed-specific promoter, and wherein the nucleic acid sequence encoding the stearoyl-ACP thioesterase polypeptide is expressed from a seed-specific promoter.

15. The method of claim 12, wherein the mutation is selected from the group consisting of a point mutation, an insertion, a deletion, a substitution, and combinations thereof.

\* \* \* \* \*

UNITED STATES PATENT AND TRADEMARK OFFICE
CERTIFICATE OF CORRECTION

PATENT NO. : 10,100,325 B2  
APPLICATION NO. : 14/815377  
DATED : October 16, 2018  
INVENTOR(S) : Thomas E. Clemente et al.

Page 1 of 1

It is certified that error appears in the above-identified patent and that said Letters Patent is hereby corrected as shown below:

On the Title Page

Item (72), Line 3, Inventors: Edgar Cahoon, delete "MN" and insert --NE--, therefor.

Signed and Sealed this  
Third Day of December, 2019

Andrei Iancu  
*Director of the United States Patent and Trademark Office*